United States Patent [19]

Broadhurst et al.

[11] Patent Number: 4,982,733
[45] Date of Patent: Jan. 8, 1991

[54] S T S (SUB-TALAR STABILIZER) ANKLE BRACE

[75] Inventors: Christopher M. Broadhurst; Peter J. Charbonneau, both of Oakville, Canada

[73] Assignee: Finlayson & Singlehurst, Canada

[21] Appl. No.: 352,899

[22] Filed: May 17, 1989

[51] Int. Cl.$^5$ .............................................. A61F 3/00
[52] U.S. Cl. ...................... 128/804; 128/166
[58] Field of Search ................ 128/804, 166, 80 E, 128/80 F

[56] References Cited

U.S. PATENT DOCUMENTS

| | | | |
|---|---|---|---|
| 1,666,290 | 4/1928 | Johnston | 128/166 |
| 2,847,991 | 8/1958 | Andrews | 128/80 E |
| 3,527,209 | 9/1970 | Baker | 128/80 E |
| 3,534,957 | 10/1970 | Norman et al. | 128/166 |
| 4,392,487 | 7/1983 | Selner et al. | 128/166 |
| 4,446,856 | 5/1984 | Jordan . | |
| 4,489,719 | 12/1984 | Lapenskie | 128/80 H |
| 4,523,394 | 6/1985 | Lindh et al. | 128/166 |
| 4,547,981 | 10/1985 | Thais et al. | 128/80 H |
| 4,556,054 | 12/1985 | Paulseth | 128/80 H |
| 4,577,419 | 3/1986 | Chassaing | 128/80 H |
| 4,646,726 | 3/1987 | Westin et al. | 128/80 H |
| 4,753,229 | 6/1988 | Sutherland | 128/166 |
| 4,817,589 | 4/1989 | Wertz | 128/80 H |

FOREIGN PATENT DOCUMENTS

| | | | |
|---|---|---|---|
| 323107 | 3/1915 | Fed. Rep. of Germany | 128/166 |
| 026682 | of 1913 | United Kingdom | 128/166 |

Primary Examiner—Edgar S. Burr
Assistant Examiner—Huong Q. Pham
Attorney, Agent, or Firm—Arnold, White & Durkee

[57] ABSTRACT

Disclosed is an ankle orthosis comprising a foot section, a cuff, and first and second flexible, non-elastic straps. The foot section has a heel portion to which an end of each strap may be secured. The cuff has material fastener elements for attaching the cuff around and over an ankle portion of a lower leg. The first strap has one end secured at the level or just forward to the base of the fifth metatarsal head and the other end secured to the cuff just forward of the fibular head. When the cuff is in operative association with an ankle, the securement of the other end of the first strap is lateral of the ankle. The tension in the first strap can be selectively adjusted. The second strap has one end secured to the heel portion rearward of the connection of the first strap therewith, and in direct line with the inferior pole of the distal fibular bone. The second strap is of a length whereby it can be wrapped around and over the Achilles tendon and at least a part of the medial portion of an ankle. The other end of the second strap is detachably secured to the cuff when the cuff is in operative association with the ankle.

9 Claims, 38 Drawing Sheets

S T S (SUB-TALAR STABILIZER) ANKLE BRACE

FIELD OF THE INVENTION

This invention relates to a supporting device for an ankle and more particularly to an ankle orthosis which stabilizes the sub-talar and talo-crural joints of the ankle.

BACKGROUND OF THE INVENTION

The ankle is a hinge joint formed by the articulations of the tibia, the malleolus of the fibula and the convex surface of the talus. Ankle injuries are relatively common injuries, particularly, as a result of athletic and sports activities.

The hind foot joints, including the metatarsal, the sub-talar and the talo-crural joints, function as a hinge to permit primarily up and down movement or bending (dorsi and plantar flexion). However, the joints also permit some turning in of the foot (inversion, a part of the supination movement) and turning out of the foot (eversion, a part of the pronation movement). The lateral malleolus (outside ankle prominence) tends to prevent excessive eversion (unless broken) but the medial malleolus (inside ankle prominence) does not prevent extended inversion to the same extent. Further the lateral (outside) ligaments are wider than medial ligaments and therefore the majority of ankle injuries occur to the outside or lateral side as a result of extended inversion.

Once severely sprained, the ankle joint is often weakened and susceptible to further injury and longer healing periods.

Taping the ankle is a common way to help protect an injured ankle but proper taping has a tendency to unduly immobilize the ankle and requires expertise that may not always be present, particularly if the tape is being changed by the injured person.

Ankle ligament protective devices or ankle orthosis are known in the art and have been developed in an attempt to provide proper support for the ankle without taping.

By way of example, Lindh et al U.S. Pat. No. 4,523,394, June 18, 1985 relates to a foot ligament protective device comprising a foot plate extending from a heel portion of the foot over at least the arch and an ankle sleeve provided with fastening means designed to be fixed around the ankle portion of the foot. Flexible, but not lengthwise extendable strap members are arranged to connect the ankle sleeve on both sides of the foot to the foot plate adjacent the heel and forward of the heel such that sideways overstretching movements of the foot are prevented.

More particularly, the Lindh et al device provides a connecting member which vertically connects the sleeve with the foot plate, the member extending generally vertically proximate the rear part of the foot plate and the heel of the foot. Another connecting member extends obliquely between the sleeve and the forepart of the foot plate. The connecting members permit foot movements through a normally full range of non-injurious positions but prevent excessive sideways movements into positions likely to cause ligament injury. The device can be worn with or without shoes.

The Paulseth U.S. Pat. No. 4,556,053, granted Dec. 3, 1985 also relates to an ankle orthosis useful for the prevention and/or rehabilitation of inversion injuries. The device includes a cuff adapted for fastening around the leg above the ankle, a foot plate for positioning beneath the foot, and connecting means extending down only the outer, lateral side of the orthosis (and foot). Resilient or elastic means may be used in conjunction with non-elastic means to produce any desired combination of elastic and non-elastic restriction of ankle inversion.

The abovementioned protective ankle devices give adequate support to the talo-crural joint but seem to have overlooked the stabilization of the sub-talar joint. Anatomically, the ankle joint is comprised of two distinct joints, those being the talo-crural and sub-talar.

The talo-crural joint is made up of the articulation between the inferior ends of the tibia and fibula and the superior articulating surface of the talus. The talo-crural joint is a compound, modified sellar joint. It has one degree of freedom; plantarflexion and dorsiflexion.

The sub-talar joint which is a compound, modified sellar joint is very important in that it allows for the inversion and eversion degree of freedom within the ankle. The anterior and posterior inferior facets of the talus articulate with the superior facets of the calcaneus to form the sub-talar joint.

The function of the sub-talar joint has been described by many authors. Downing, Klein and D'Amico state that ". . . , since no musculature attaches to it, the talus essentially functions as a 'contoured ball bearing' allowing motion to occur concurrently between itself and the four bones with which it articulates" (Downing, J. W., Klein, S. J., D'Amico, J. C., The Axis of Motion of the Rearfoot Complex, J. Amer. Pod. Assoc., Vol. 68, No. 7, July 1978, 484-499). Therefore the talo-crural and sub-talar joints can be thought of as acting together as a functional complex.

It is known by those in the field that the combination of ankle inversion (sub-talar joint) and plantar flexion (talo-crural joint) during bearing leads to a typical ankle sprain.

Accordingly, there is a need for a new orthosis device which will adequately stabilize the sub-talar as well as the talo-crural joints of the ankle and prevent inversion of the ankle with minimal limitation to, other movements within the joints including plantar flexion.

SUMMARY OF THE INVENTION

The invention seeks to provide a novel orthosis or ankle brace which emphasizes the stabilization of the sub-talar as well as the talo-crural joints of the ankle. This is accomplished by straps which are adapted to be specifically positioned to prevent or reduce inversion of the ankle with minimal limitation of other movements within the joint.

More particularly the novel brace gives support to the sub-talar joint through a second stabilizing strap which encircles the ankle in a posterio-medial direction. The attachments of this strap aid in the support of the lateral structures of the ankle which includes the calcaneo-fibular and lateral talo-calcaneal ligaments. The main function of this strap is to prevent excessive inversion from occurring at the sub-talar joint and limit the translation movement of the ankle.

The invention broadly pertains to an ankle orthosis comprising a foot section, a cuff, and first and second flexible, non-elastic strap means. The foot section has a heel portion including means by which an end of each strap means may be secured thereto. The cuff has fastening means for attaching the cuff around and over an ankle portion of a lower leg. The first strap means has one end secured to a forward, lateral part of the heel portion and the other end secured to the cuff such that when the cuff is in operative association with an ankle, the securement of the other end of the first strap means is lateral of the ankle. There is means for selectively adjusting tension in the first strap means. The second strap means has one end secured to the heel portion rearward of the connection of the first strap means therewith. The second strap means is of a length whereby it can be wrapped around and over the Achilles tendon and at least a part of the medial portion of an ankle. Means are provided for detachably securing the other end of the second strap means to the cuff when the cuff is in operative association with the ankle.

More particularly, the first strap has one end secured to the heel portion so that with respect to the user, the one end is secured substantially at a level or just forward to the base of the fifth metatarsal head. The other end of the strap is secured to the cuff so that when in use, the securement is generally just forward of the fibula head of the ankle. The end of the second strap secured to the heel portion is secured so that in use the securement is substantially in line with the inferior pole of the distal fibular bone.

Preferably the second strap means includes relatively slidable protective cover means over the portion thereof adapted to be wrapped around and over the Achilles tendon.

The cuff preferably has opposed ends with material fastening means whereby the cuff is secured about an ankle with the material fastening means on the medial portion of an ankle, generally opposite the connection of the first strap means with the cuff.

Further, the means for securing the other end of the second strap means to the cuff section is preferably at an anterior location of an ankle when the cuff is in operative association therewith.

Other aspects, features and advantages of the invention will become further apparent from the detailed description of the invention herein.

DESCRIPTION OF THE PREFERRED EMBODIMENT

Figure 1:
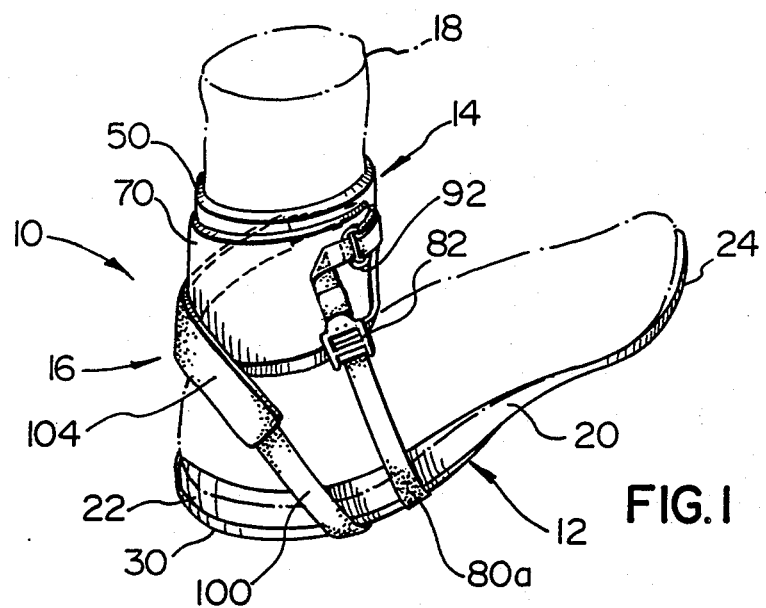
FIG. 1 is a rear perspective view of the orthosis device with an ankle shown in dotted lines. Although the device is worn with a shoe, the shoe is not shown for purposes of clarity.
Figure 2:
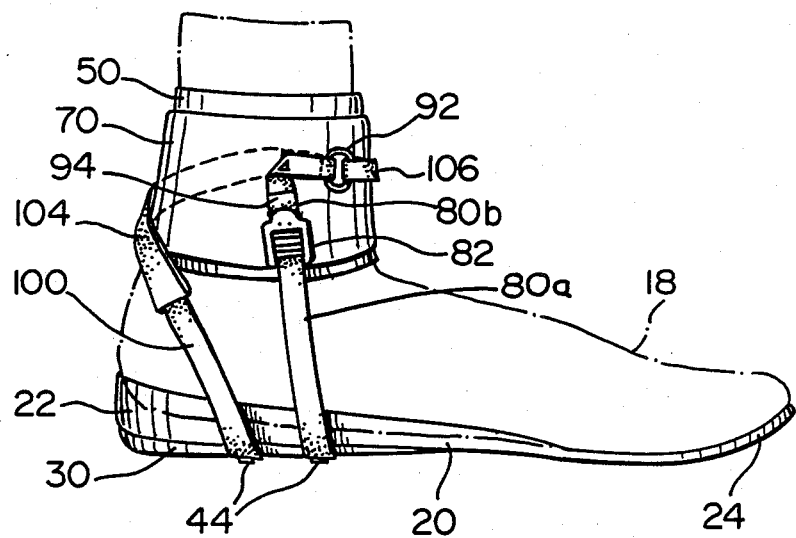
FIG. 2 is a lateral side view of the device.
Figure 3:
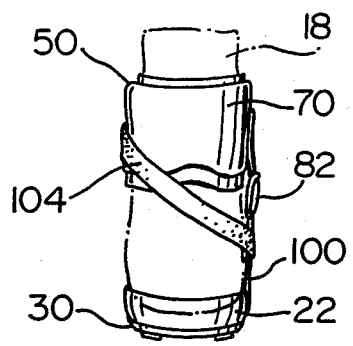
FIG. 3 is a rear view of the device.

Turning to the drawings, there is shown the new orthosis 10 which comprises a foot section 12, a cuff section 14 and a strap assembly 16 which interconnects cuff section 14 and foot section 12 as more particularly set out herein. A foot 18 is shown in dotted lines in several of the Figures. Although the brace is worn with a shoe, the shoe is not shown for reasons of simplifying the illustration of the brace.

Figure 4:
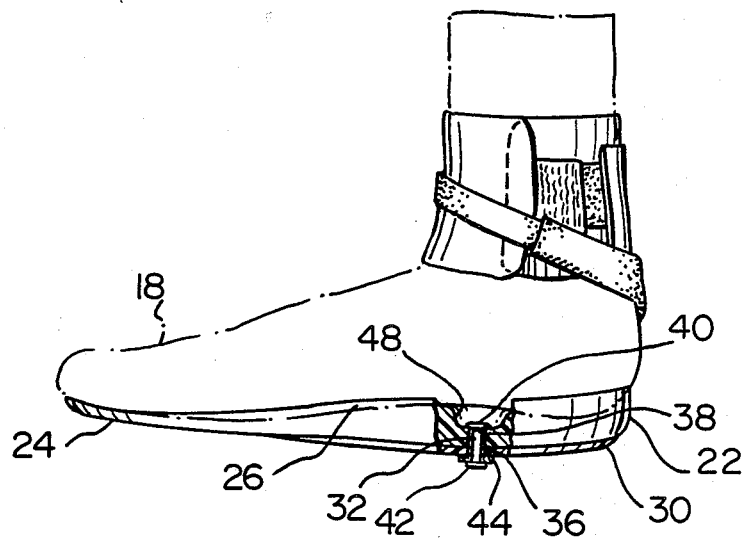
FIG. 4 is a partial sectional, medial view of the device.

Foot section 12 comprises full orthotic insole 20 of polypropylene material with nylon cloth upper, commonly available in the market. The insole has heel portion or heel cup 22 with its slightly upwardly curved periphery, toe portion 24 and arch portion 26 (FIG. 4). Insole 20 is of the type which is adapted for use in shoes to provide added comfort to the wearer and the toe portion 24 in particular, can be trimmed to better fit within selected shoes.

Relatively hard stiff plastic (polypropylene) heel plate 30 is attached to the insole 20 by rivets 32, four rivets being shown. Each rivet passes through a hole 36 (see FIG. 4) in plate 30 and hole 38 in insole 20. Head 40 of rivet 32 is rounded and the shank end 42 is pressed or turned over washer 44, the rivet being attached sufficiently tightly that head 40 is effectively sunk at 48 into the upper surface of insole 20 and is not felt by the wearer of device 10. Plate 30 runs from the area of heel cup 22 of insole 20 to just in front of mid foot area or region.

As will become more apparent herein, rivets 32 are also used to secure strap assembly 16 to plate 30 (and insole 20).

Figure 5:
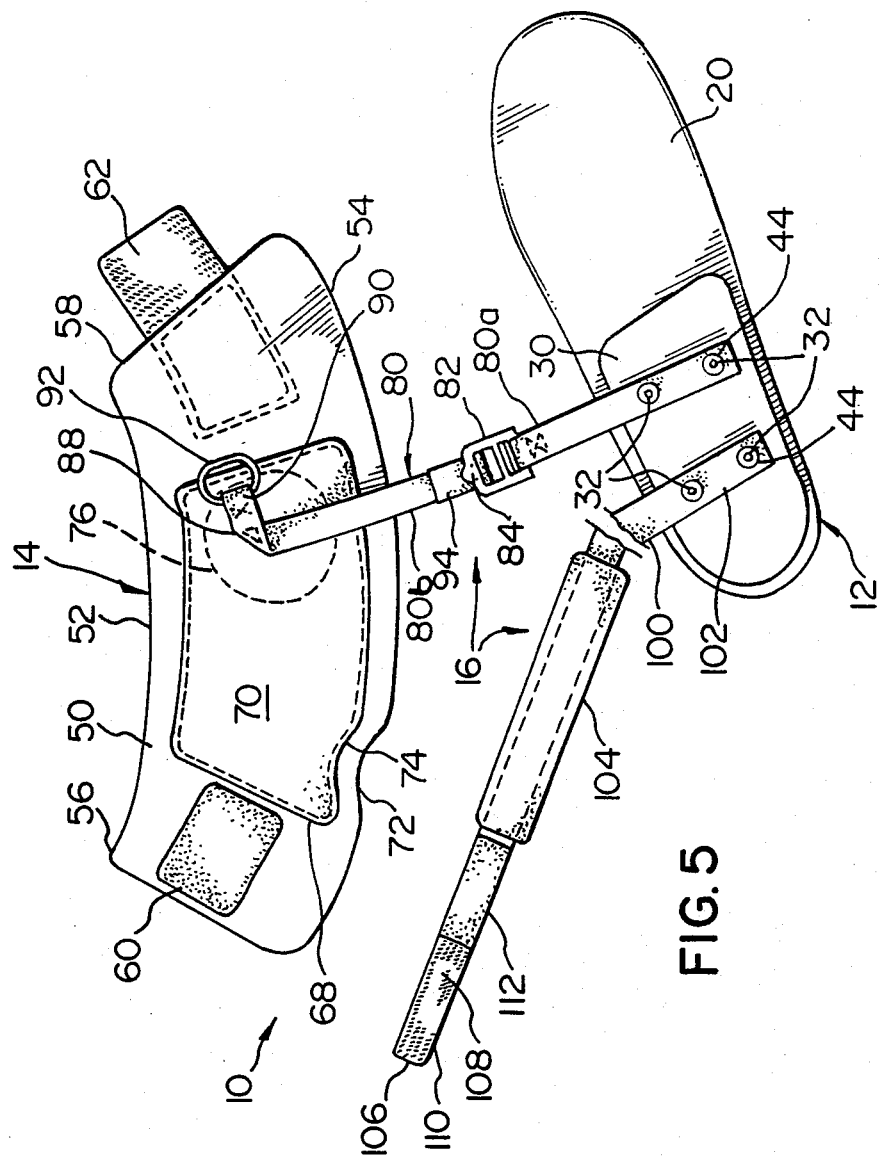
FIG. 5 is a lay out view of the device.

Cuff section 14 is cloth covered Neoprene ® material, and is shown in FIG. 5 in lay-out fashion along with strap assembly 16 and the underside or bottom or foot section 12.

Cuff section 14 comprises cuff 50 having opposed curved sides 52 and 54 and opposed ends 56 and 58. Attached to cuff 50 at ends 56 and 58 is material fastener elements 60 (pile aspect) and 62 (hook aspect) of the type marketed under the trade mark VELCRO ®. Sewn at 68 to cuff 50 is outer, reinforcing layer of Neoprene ® material 70 which has a peripheral contour similar to that of cuff 50 along cuff edges 52 and 54. Notches 72 and 74 in cuff 50 and layer 70 are adapted to align with and fit about the upper portion of the Achilles tendon when the device is in operative association with an ankle. Layer 70 also provides additional padding to cuff 50 and within the area defined by layer 70 is area 76 (shown in dotted line, FIG. 5) which has still further padding and reinforcement material adapted to fit over the outer "ankle bone" protrusion or the lateral malleolus. Area 76 also provides additional means for reinforcing the attachment of strap means referred to further herein.

Strap assembly 16 comprises an anterio-lateral strap 80 of nylon material which in use runs in an upwardly slightly rearwardly direction. Strap 80 has plate portion 80a and cuff portion 80b. Strap portion 80a is secured by rivets 32 to plate 30 (and insole 20). Commonly available plastic buckle 82 having release tab 84 is connected to other or free end 86 of portion 80a. Strap portion 80b is secured by stitching 88 to cuff 50 at point short of cuff end 92. Stitching at 88 goes right through layer 70, the additional reinforcing material in area 76 and cuff 50 in order to provide a secure connection between strap portion 80b and cuff 50. In sewing strap portion 80b at 88 to cuff 50, it is twisted approximately 90° and ring buckle element 92 is securely connected to cuff end 88 of strap portion 80b, the end and buckle being aligned generally with fastener material 62. End 94 of strap portion 80b is detachably connected in known fashion with buckle 82 and may be pulled upwardly to shorten or tighten strap 80. Pushing on buckle tab 84 releases tension in strap 80.

A posterio-medial or heel lock strap 100 of nylon material has one end 102 secured to foot plate 30 (and insole 20) by rivets 32 as shown particularly in FIG. 5 and has protective cover 104 made of nylon cloth covered Neoprene ® similar to that of cuff 50. Cover 104 is slidable on strap 100 and although shorter than strap 100 is preferably at least ½ the length of strap 100. The end 106 of strap 100 has material fastener means 108 comprising of hook 118 and pile 112 portions so that when end 106 is threaded through buckle 92, the end 106 may be folded back upon itself and secured to itself through the material fastener 108. In use, strap 100 extends from the posterio-lateral aspect of the foot, around the heel and in an upward and forward direction along the inside or medial portion of the ankle.

In use, a person with a sprained ankle would remove the insole from appropriate ones of a selected pair of shoes and insert insole 20 of device 10 into the appropriate shoe (trimming around the toe area 26 as may be necessary). The shoe is laced up about the foot, preferably over a sock. Cuff 50 is then wrapped around the leg (and sock) just above or superior the ankle bone (malleolar prominena) making sure the notches 72/74 are aligned with the Achilles tendon. Cuff 50 is then secured firmly about the leg with the VELCRO® fastener elements 60 and 62.

The user then places the foot, with shoe on, in a slightly everted and flexed position, i.e. the outside of the foot and toes are lifted or raised up. The posterio-medial strap 100 (the second or long strap) with its cover 104 is laid around the back of the heel (making sure the cover 104 is over the heel portion) and along the inside of the ankle to the front of the ankle. End 106 is threaded through cuff buckle 92 and turned back on itself. Material fastener elements 110 and 112 are appropriately secured.

While the everted and flexed position is maintained, end 94 of portion 80b of anterio-lateral (or first) strap is pulled up to tighten strap 80 until the desired amount of stability is attained. If the person's normal walking gait is altered, strap 80 may be loosened as desired by pushing on tab 84.

Although rivets 32 and washers 44 protrude from the bottom of plastic plate 30, they do not do so to an extent that affects the comfort or adversely affects the insole of a shoe with which the device is worn.

It will be appreciated that various sized devices or braces will be required to meet the demands of different sized feet. However, the device is designed so that in use, the first end or plate portion 80a of strap 80 as secured to heel plate 30 will be substantially at the level or just forward to the base of the fifth metatarsal head of the foot and the other end or cuff portions 80b of strap 80 will be generally just forward of the fibular head of the user's ankle. The second or lock strap 100 has end 102 connected to heel plate 30 so that in use, end 102 is substantially in line with the inferior pole of the distal fibular bone.

In packaging the device for market, a second like insole 20 with riveted plastic heel plate 30 (without straps and cuffs) would be included so that the use of device 10 will not cause any limb length discrepancy.

Variations and modifications of the invention will be apparent to those skilled in the art. Although materials have been previously indicated, such as Neoprene® for cuff section 12 and protective strap cover 104, other materials may obviously be used which provide the desired degree of strength and comfort.

Moreover although nylon material has been indicated for straps 80 and 100, any other strap material which is essentially non-elastic, but flexible, may be used. Still further, other fastening means are possible, particularly with respect to adjustable buckle means 82. Obviously strap portion 80a could have material fastener means such as VELCRO® strap portion 80b having a circular or box ring (similar to ring 92) securely attached thereto.

The embodiments of the invention in which an exclusive property or privilege is claimed are defined as follows:

1. An ankle orthosis comprising:
 a foot section, a cuff, a first and second flexible, non-elastic strap means;
 said foot section, having a heel portion including means by which an end of each said strap means may be connected thereto;
 said cuff having fastening means for attaching the cuff around and over an ankle portion of a lower leg;
 said first strap means having one end connected to a forward, lateral part of said heel portion such that in use said one end is generally at or just forward of the base of the fifth metatarsal head of a user's foot, the other end of the first strap means being secured to said cuff such that when the cuff is in operative association with an ankle, said first strap means substantially crosses over the anterior talo fibular ligament of the ankle and the other end of said first strap means is secured to said cuff slightly anterior of the fibular head of the user's ankle; means for selectively adjusting tension in said first strap means;
 said second strap means having one end connected to said heel portion rearward of the connection of said first strap means therewith, and generally in line with the inferior pole of the distal fibular bone of the user's foot, said second strap means being of a length whereby said second strap means can be wrapped around and over the Achilles tendon of the ankle and at least a part of the medial portion of the ankle; and means for detachably securing the other end of said second strap means to said cuff forward of the medial portion of the ankle when said cuff is in operative association therewith.

2. The ankle orthosis of claim 1 wherein said second strap means includes relatively slidable protective cover means over the portion thereof adapted to be wrapped around and over the Achilles tendon.

3. The ankle orthosis of claim 2 wherein said cuff has opposed ends with material fastening means associated therewith, whereby said cuff is secured about an ankle with said material fastening means on the medial portion of an ankle, generally opposite the connection of said first strap means with said cuff.

4. The ankle orthosis of claim 3 wherein said means for securing the other end of said second strap means to said cuff section is at an anterior location of an ankle when said cuff is in operative association therewith.

5. The ankle orthosis of claim 4 wherein said cuff section includes ring fastener means at said location and said second strap means has material fastener means associated with its other end whereby said other end is secured about said ring fastener means.

6. The ankle orthosis of claim 5 wherein said means for adjusting tension in said first strap means includes buckle means.

7. The ankle orthosis of claim 5 wherein the other end of said first strap means includes means to which said ring fastener means is attached.

8. The ankle orthosis of claim 5 wherein said cuff is reinforced and padded in the area where said first strap means and ring fastener means are connected to said cuff.

9. The ankle orthosis of claim 8 wherein said reinforced area includes padding over the part of said cuff which encircles the heel of a foot when said cuff is in operative association therewith.

* * * * *

UNITED STATES PATENT AND TRADEMARK OFFICE
CERTIFICATE OF CORRECTION

PATENT NO.   :   4,982,733

DATED        :   January 8, 1991

INVENTOR(S)  :   Christopher M. Broadhurst and Peter J. Charbonneau

It is certified that error appears in the above-identified patent and that said Letters Patent is hereby corrected as shown below:

On title page, at item [73] Assignee, cancel
     "Finlayson & Singlehurst, Canada"

On title page, following the Abstract,
     cancel "38" and insert "3"
     before "Drawing Sheets"

Signed and Sealed this

Fourteenth Day of July, 1992

*Attest:*

DOUGLAS B. COMER

*Attesting Officer*     Acting Commissioner of Patents and Trademarks